United States Patent
Duddy et al.

(10) Patent No.: US 9,144,619 B2
(45) Date of Patent: Sep. 29, 2015

(54) MEDICAL INSTRUMENT STERILIZATION SYSTEM AND METHOD

(75) Inventors: Christopher Roy Duddy, Londonderry, NH (US); Tony Foley, Manchester, NH (US); Gary T. Dane, Bow, NH (US)

(73) Assignee: Symmetry Medical Manufacturing, Inc., Warsaw, IN (US)

(*) Notice: Subject to any disclaimer, the term of this patent is extended or adjusted under 35 U.S.C. 154(b) by 693 days.

(21) Appl. No.: 13/364,670

(22) Filed: Feb. 2, 2012

(65) Prior Publication Data

US 2012/0195792 A1    Aug. 2, 2012

Related U.S. Application Data

(60) Provisional application No. 61/438,724, filed on Feb. 2, 2011.

(51) Int. Cl.
*A61L 2/16* (2006.01)
*A61L 2/26* (2006.01)

(52) U.S. Cl.
CPC ............. *A61L 2/26* (2013.01); *A61L 2202/182* (2013.01); *A61L 2202/24* (2013.01)

(58) Field of Classification Search
CPC ....... A61L 2/20; A61L 2/26; A61L 2202/182; A61L 2202/24

USPC .................... 206/439; 220/528; 422/300, 297
See application file for complete search history.

(56) References Cited

U.S. PATENT DOCUMENTS

| | | | |
|---|---|---|---|
| 7,320,405 B2 * | 1/2008 | Stahl | 206/509 |
| 2003/0118491 A1 * | 6/2003 | Frieze et al. | 422/297 |
| 2004/0144670 A1 * | 7/2004 | Riley | 206/370 |
| 2009/0250420 A1 * | 10/2009 | Martin et al. | 211/134 |

* cited by examiner

*Primary Examiner* — Sean E Conley
*Assistant Examiner* — Donald Spamer
(74) *Attorney, Agent, or Firm* — Hayes Soloway PC

(57) ABSTRACT

A medical instrument sterilization system and method is provided. The system includes a sterilization container having a first container portion engagable with a second container portion to enclose an interior compartment from an exterior atmosphere. At least one insert is locatable within the interior compartment of the sterilization container, the at least one insert having a medical instrument holding area surrounded by a plurality of sidewalls, wherein the medical instrument holding area is sized to hold at least one medical instrument. A filter is secured within a wall of the first container portion, wherein the filter is in communication with the interior compartment and the exterior atmosphere.

11 Claims, 9 Drawing Sheets

MEDICAL INSTRUMENT STERILIZATION SYSTEM AND METHOD

CROSS REFERENCE TO RELATED APPLICATION

This application claims benefit of U.S. Provisional Application Ser. No. 61/438,724, entitled, "Medical Instrument Sterilization System and Method" filed Feb. 2, 2011, the entire disclosure of which is incorporated herein by reference.

FIELD OF THE DISCLOSURE

The present disclosure is generally related to sterilization systems and more particularly is related to a medical instrument sterilization system and method.

BACKGROUND OF THE DISCLOSURE

Traditionally, medical instrument sterilization cases are constructed with holes formed along the entirety of the surface. The cases are sometimes placed within sterilization containers during sterilization processes, while the medical instruments are housed in trays within the cases. Sometimes the trays have inserts/platforms mounted therein with instrument holders mounted to the platforms. Conventionally, the sterilization cases may be put into autoclaves by either wrapping the cases in a non-woven polymeric filter material or by placing a sterilized case in sterilization containers that are near airtight after a sterilization process. These conventional containers are generally airtight, except for one or two controlled sections where filters are affixed.

Commonly, the filters on the conventional containers are air and water permeable. When the filters are dry, microorganisms cannot penetrate the filter, but when the filters become wet, microorganisms, bacteria and cleaning solutions can permeate the filter. Thus, a sterilized case with sterilized medical instruments therein, that is placed within a container, may stay sterilized as long as the filter remains dry and secure. Similarly, a sterilized case wrapped in a filter material may stay sterilized, so long as the filter material isn't compromised or removed. However, the wrapped filter material can only provide a reliable sterile barrier for about two weeks and the conventional container with a filter affixed can only provide the sterile barrier for six months. The sterile environment is not compromised until the container, and the sterilization case having the sterilization tray with medical instruments are in the operating room for use. With operating room space at a premium, there is a significant amount of packaging taking up space in one operating room.

Thus, a heretofore unaddressed need exists in the industry to address the aforementioned deficiencies and inadequacies.

SUMMARY OF THE DISCLOSURE

Embodiments of the present disclosure provide a system and method for a medical instrument sterilization system. Briefly described, in architecture, one embodiment of the system, among others, can be implemented as follows. The system includes a sterilization container having a first container portion engagable with a second container portion to enclose an interior compartment from an exterior atmosphere. At least one insert is locatable within the interior compartment of the sterilization container, the at least one insert having a medical instrument holding area surrounded by a plurality of sidewalls, wherein the medical instrument holding area is sized to hold at least one medical instrument. A filter is secured within a wall of the first container portion, wherein the filter is in communication with the interior compartment and the exterior atmosphere.

The present disclosure can also be viewed as providing a medical instrument sterilization system. In this regard, one embodiment of such a system, among others, can be implemented as follows: A sterilization container has a first container portion engagable with a second container portion to enclose an interior compartment from an exterior atmosphere. At least a first and a second insert are positioned within the interior compartment of the sterilization container, wherein the first insert is positioned to nest on top of the second insert, wherein each of the first and second inserts have a medical instrument holding area surrounded by a plurality of sidewalls, wherein the medical instrument holding areas are sized to hold at least one medical instrument. A stabilizing structure is coupled to the first insert and rising above each of the plurality of sidewalls of the first insert. A foot structure is positioned on a bottom of the second insert, wherein the stabilizing structure and the foot structure contact the first container portion and the second container portion, respectively, to stabilize the first and second inserts within the interior compartment. A filter is secured within a wall of the first container portion, wherein the filter is in communication with the interior compartment and the exterior atmosphere.

The present disclosure can also be viewed as providing methods of sterilizing a medical instrument with a medical instrument sterilization system. In this regard, one embodiment of such a method, among others, can be broadly summarized by the following steps: placing a medical instrument within a first insert, the first insert having a medical instrument holding area and a plurality of sidewalls; positioning the first insert within an interior compartment of a sterilization container, the sterilization container having a first container portion engagable with a second container portion to enclose the interior compartment from an exterior atmosphere; sealing the first container portion to the second container portion; subjecting the sterilization container with the first insert inside the interior compartment to a moist sterilization process within a sterilization environment, whereby a quantity of sterilization material moves from the exterior atmosphere through a filter secured within a wall of the first container portion to the interior compartment to sterilize the medical instrument; and drying the sterilization container and the filter secured therein without removing the sterilization container from the sterilization environment, thereby providing a sterilized interior compartment after moist sterilization process.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
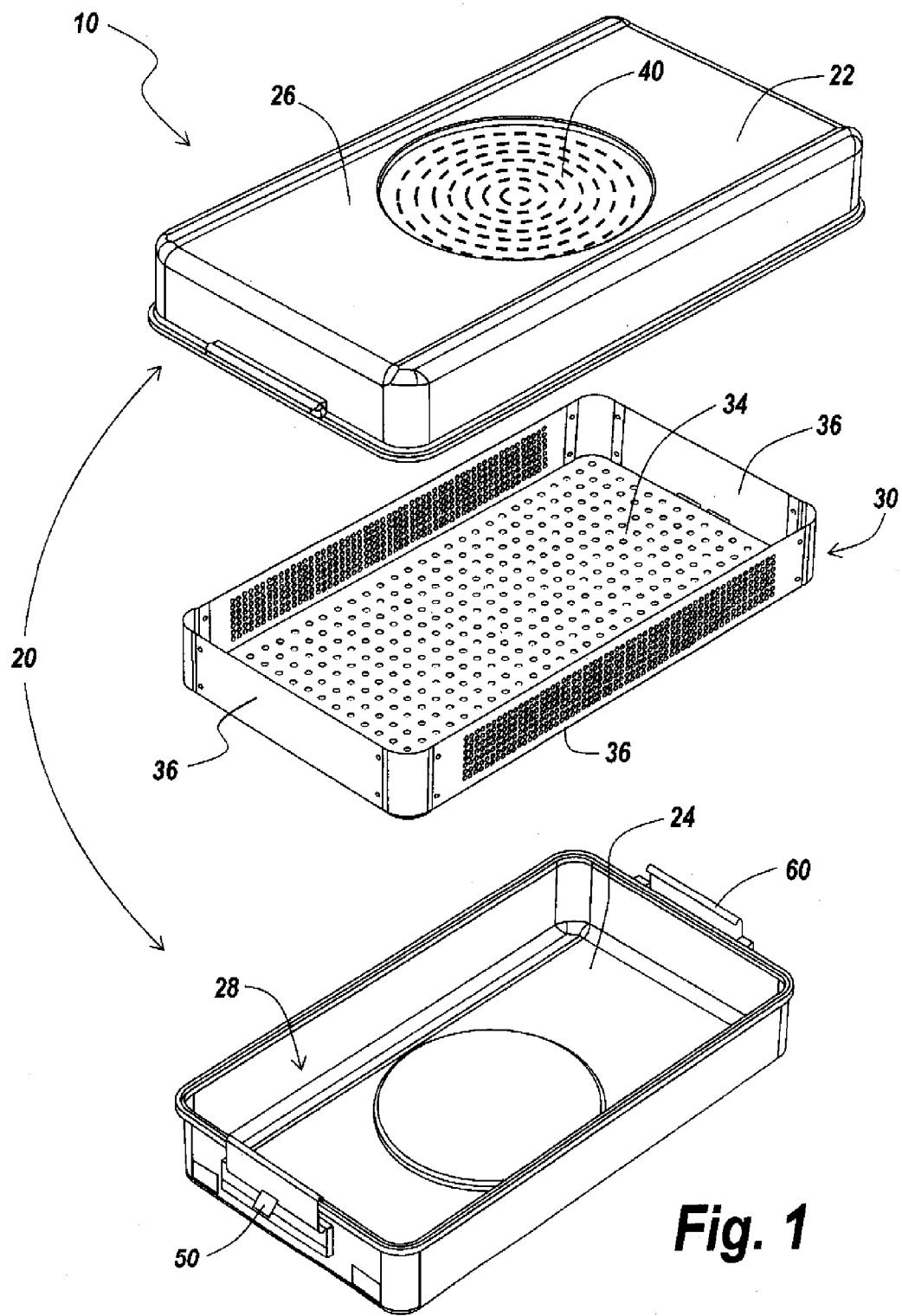
FIG. 1 is an exploded view illustration of a medical instrument sterilization system, in accordance with a first exemplary embodiment of the present disclosure.

FIG. 1 is an exploded view illustration of medical instrument sterilization system 10, in accordance with a first exemplary embodiment of the present disclosure. The medical instrument sterilization system 10, which may also be referred to as the system 10, includes a sterilization container 20 having a first container portion 22 engagable with a second container portion 24. The first and second container portions 22, 24 may be engagable to enclose an interior compartment 28 from an exterior atmosphere, which is exterior to the sterilization container 20. At least one insert 30 is locatable within the interior compartment 28 of the sterilization container 20. The at least one insert 30 has a medical instrument holding area 34 surrounded by a plurality of sidewalls 36, wherein the medical instrument holding area 34 is sized to hold at least one medical instrument (not shown). A filter 40 is secured within a wall 26 of the first container portion 22, wherein the filter 40 is in communication with the interior compartment 28 and the exterior atmosphere.

The system 10 may be used for sterilizing any medical instrument, such as those commonly used in surgeries or other medical procedures. Any type of medical instrument may be sterilized within the system 10, and the system 10 may be used in any medical setting. This includes doctors offices, outpatient centers, surgical facilities, hospitals and in emergency medical areas, like disaster relief centers. Additionally, the system 10 may be used in off-site sterilization centers that support a medical facility, wherein sterilized medical instruments are provided to the medical facility. The system 10 may be sterilized in a variety of sterilization environments, commonly an autoclave, or any other device that sterilizes a medical instrument by subjecting it to a high pressure saturated steam at a high temperature.

The sterilization container 20 may be any size or shape, and may have any configuration. As is illustrated in the exploded view of FIG. 1, the sterilization container 20 may have a first container portion 22 that is engagable with a second container portion 24. This may include configurations where the first container portion 22 is a lid, or upper cover, and the second container portion 24 is a base, or lower unit. Other designs are also envisioned. These include designs where the first container portion 22 is a substantially enclosed structure and the second container portion 24 is a door or opening. The sterilization container 20 may be manipulated to create and allow access to an interior portion of the sterilization container 20, to insert or remove the insert 30, or a medical instrument housed therein. This may be accomplished simply by engaging and disengaging the first container portion 22 from the second container portion 24 with a container latch 50.

In accordance with this disclosure, the interior compartment 28 of the sterilization container 20 may be characterized as the interior environment of the sterilization container 20, when the sterilization container 20 is substantially enclosed. In other words, when the first container portion 22 and the second container portion 24 are engaged together, the interior compartment 28 is formed therebetween. The interior compartment 28 is secluded from the environment exterior to the sterilization container 20, i.e., the exterior atmosphere, thereby allowing a sterilized environment to be created within the interior compartment 28. Accordingly, the sterilization container 20 may create a fully impenetrable barrier between the interior atmosphere and the exterior atmosphere, wherein only the filter 40 permits a transmission of a gas, substance or other object between the interior atmosphere and the exterior atmosphere when the first and second container portions 22, 24 are engaged together.

The insert 30, which may be any type of medical instrument tray or holding structure, is mounted, either permanently or removably, to the sterilization container 20 and is positioned within the interior compartment 28. As is discussed with respect to the second exemplary embodiment, more than one insert 30 may be used within the system 10. The insert 30 may house or hold any type of medical instrument before, during and after the sterilization process. The insert 30 may include perforated or porous surfaces, cutout holes and apertures, and have any type of design. For example, as is shown in FIG. 1, the insert 30 may have a medical instrument holding area 34 that is surrounded by a plurality of sidewalls 36, thereby creating a 5-sided structure. This design may be preferable because the access can be gained to the medical instrument holding area 34 through the upper surface area 32 of the insert 30.

The upper surface area 32 may be characterized as the open side of the insert 30, i.e., the side of the insert 30 that does not have a sidewall 36 or medical instrument holding area 34. Variations may include a flat-planar design, or a substantially planar design with a partial side. However, it is preferable for the insert 30 to not have any covering, surface or other substantially covering structure on an upper surface area 32, and thus to be fully open. The open upper surface area 32 may allow the insert 30, and any medical instruments housed therein, to be entirely exposed to the interior compartment 28 of the sterilization container 20, which ensures that the proper sterilization can be achieved.

A filter 40 is secured within a wall 26 of the first container portion 22, between the interior compartment 28 and the exterior atmosphere. The filter 40 may include a variety of filters and filtering devices, such as air and water permeable filters. The filter 40 may allow a waterborne sterilization material to pass through the wall of the sterilization container 20, via the filter 40, when in a sterilization environment, but prevent any substance or microorganism from gaining access to the interior of the sterilization container 20. One way of accomplishing this is with a filter 40 that is both air and water permeable.

The filter 40 may function by allowing sterilization substances within an autoclave to pass through the filter 40 when it is wet, but prevent any substances, bacteria or microorganisms from passing through the filter 40 when it is dry. This may be referred to as a 'wet-functioning' filter 40. Accordingly, when the filter 40 is moistened during a sterilization process, the sterilization substances, as well as other substance such as microorganisms, may pass through the filter 40. The sterilization substances act to sterilize the interior atmosphere of the sterilization container 20 throughout the sterilization process, and once fully sterilized, the filter 40 becomes dry. Normally, the filter 40 may dry out from the high heat temperatures and/or low moisture content within the autoclave towards the end of the sterilization process. Prior to removing the sterilization container 20 from the autoclave, the filter 40 is fully dry, and therefore no bacteria, microorganism or other unsterile substance can pass through the filter 40. The system 10 may then be stored for any period of time, such as up to 180 days or longer, till the medical instruments within the system 10 are needed.

The filter 40 may be reusable, or disposable after a certain number of uses. Additionally, the system 10 may include more than one filter 40, depending on the type of sterilization process. For example, only one filter 40 may be included positioned against or abutting a perforated area of the first container portion 22 when a vacuum based sterilization process is used. Accordingly, the vacuum based sterilization process will sterilize the medical instruments within the system 10 and remove the sterilization material within the sterilization container 20 during the sterilization process. Other configurations with the filter 40 may be used with the system 10, including a single sterilization container 20 with two filters 40, as is described with respect to FIG. 8.

In use, the system 10 may be used to sterilize medical instruments and store sterilized medical instruments until they are needed for use in a medical procedure. For example, non-sterile medical instruments may be placed within the insert 30, which may be placed within the interior compartment 28 between the first and second container portions 22, 24. The sterilization container 20 may then be placed within a sterilization environment, such as an autoclave, where it is subjected to a moist sterilization process, such as any sterilization process that involves humid conditions or a liquid sterilant. The sterilization process will moisten the filter 40, which will allow the sterilization material to pass through it and enter the interior compartment 28. Once inside, the sterilization material will sterilize the medical instruments.

After the medical instruments are sterile, the sterilization material may be removed from the sterilization container 20 and the sterilization environment may be transitioned to a dry environment. Over a period of time within the dry sterilization environment, the filter 40 will dry out, thus preventing any material from passing through it. When this is achieved, the sterilization container 20 may be removed from the sterilization environment and stored for later use. The medical instruments within the sterilization container 20 will remain sterilized so long as the first and second container portions 22, 24 are engaged together and the filter 40 remains dry. The system 10 may keep the medical instruments sterile for any period of time until they are needed for a medical procedure. For example, the system 10 may keep the interior compartment 28 of the sterilization container 20 sterile for 7, 14, 30, 60, 90, or 180 days, or more.

Figure 2:
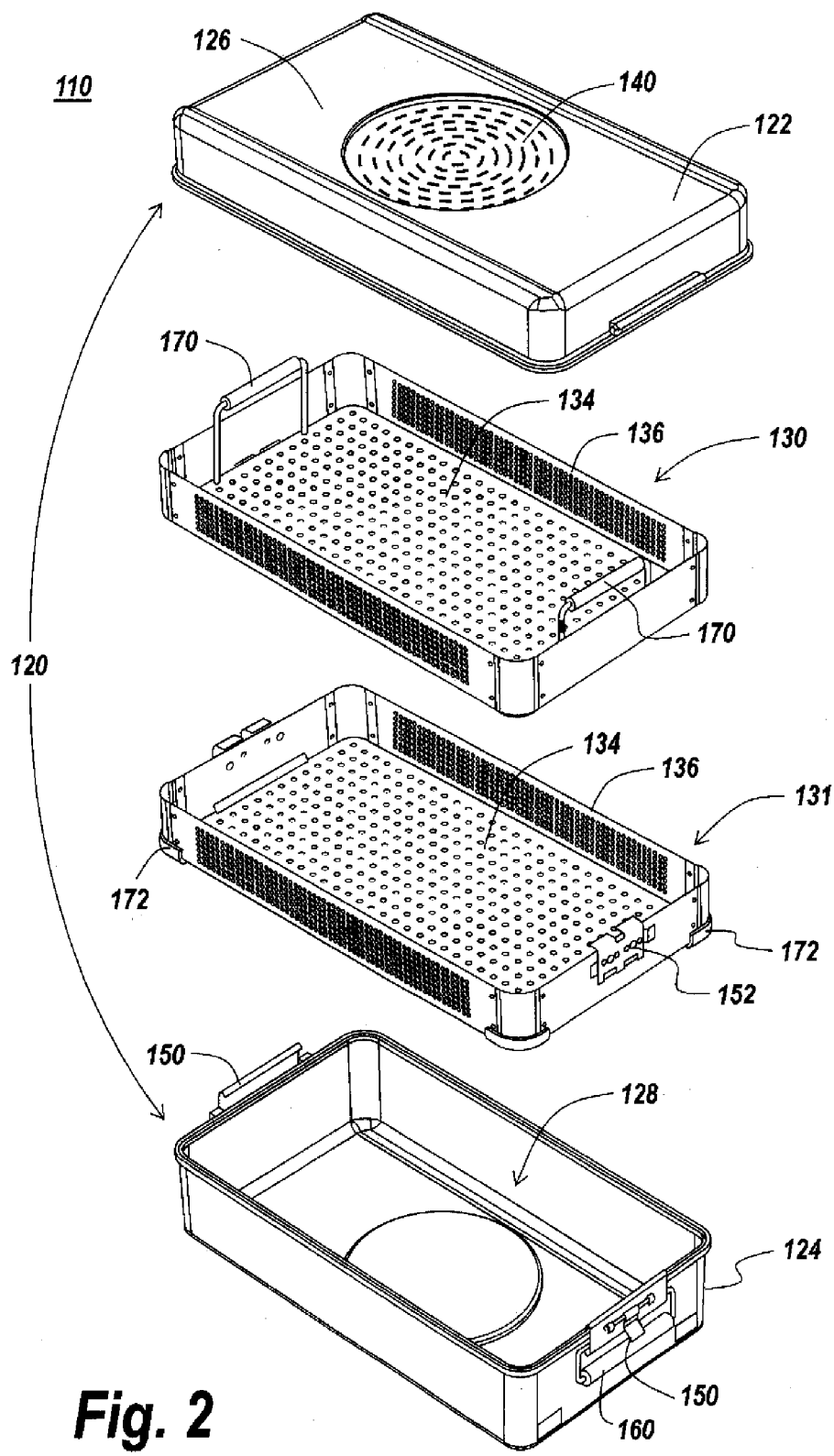
FIG. 2 is an exploded view illustration of a medical instrument sterilization system, in accordance with a second exemplary embodiment of the present disclosure.

FIG. 2 is an exploded view illustration of a medical instrument sterilization system 110, in accordance with a second exemplary embodiment of the present disclosure. The medical sterilization system 110 is substantially similar to the system 10 of the first exemplary embodiment, as described with respect to FIG. 1. Accordingly, any of the elements, features and/or configurations described with respect to the first exemplary embodiment, or with respect to any other embodiment described herein, may be included in this second exemplary embodiment. The medical sterilization system 110, which may be referred to simply as 'system 110' includes a sterilization container 120 having a first container portion 122 engagable with a second container portion 124. The first and second container portions 122, 124 may be engagable to enclose an interior compartment 128 from an exterior atmosphere, which is exterior to the sterilization container 120. At least a first and a second insert 130, 131 are both locatable within the interior compartment 128 of the sterilization container 120, wherein the first insert 130 is nested on the second insert 131 (shown in detail in FIG. 3). Both of the first and second inserts 130, 131 have a medical instrument holding areas 134 surrounded by a plurality of sidewalls 136, wherein the medical instrument holding area 134 is sized to hold at least one medical instrument (not shown). A filter 140 is secured within a wall 126 of the first container portion 122, wherein the filter 140 is in communication with the interior compartment 128 and the exterior atmosphere.

Figure 3:
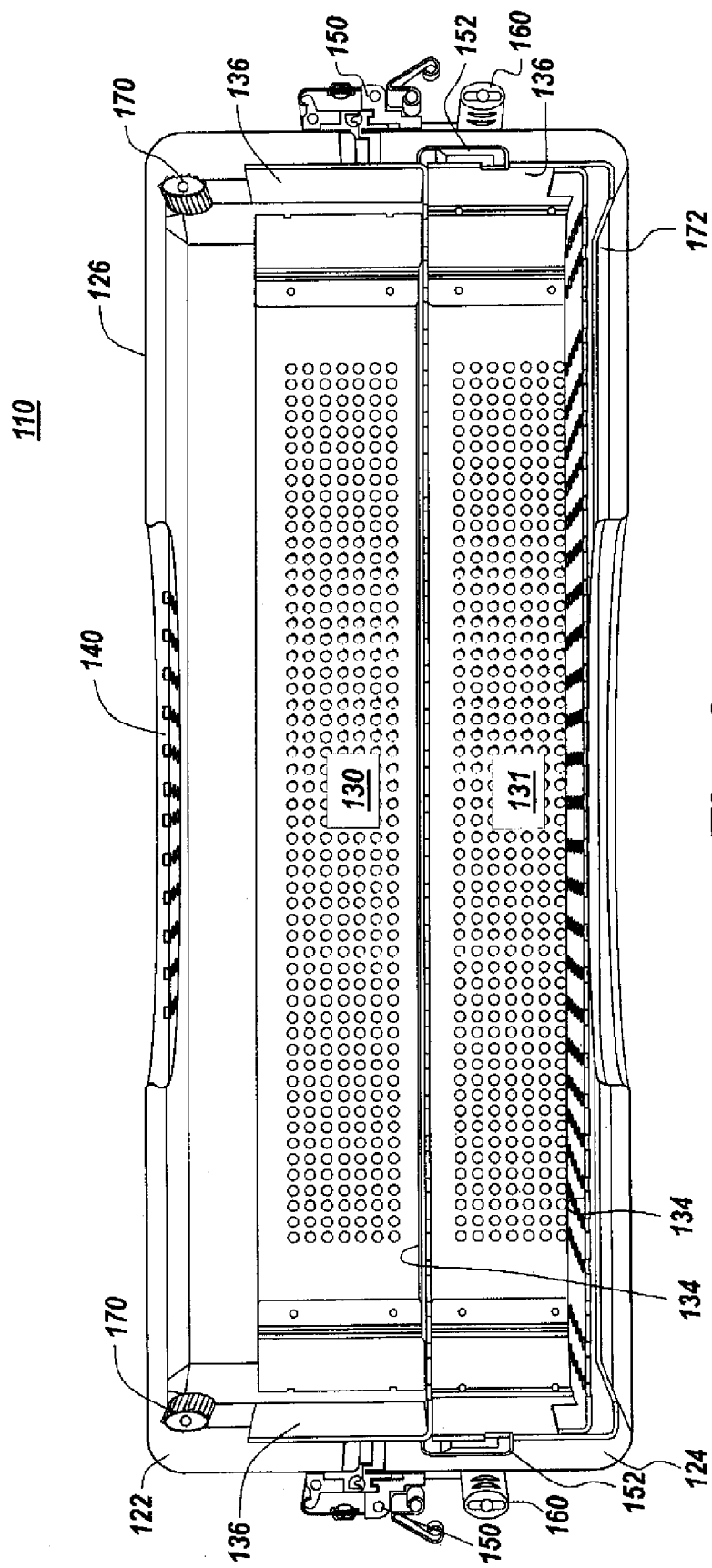
FIG. 3 is a side cross-sectional view illustration of the medical instrument sterilization system, in accordance with the second exemplary embodiment of the present disclosure.

FIG. 3 is a side cross-sectional view illustration of the medical instrument sterilization system 110, in accordance with the second exemplary embodiment of the present disclosure. The system 110 may include two or more inserts, including at least a first and second insert 130, 131, that are positioned vertical to one another. Both of the first and second inserts 130, 131 may house medical instruments during a sterilization process, wherein sterilization material contacts the medical instruments via a plurality of perforations in the first and second inserts 130, 131. When the first and second inserts 130, 131 are used, as illustrated in FIG. 3, the first insert 130, which is positioned on top of the second insert 131, may have a fully open upper surface area 132. The second insert 131, and any subsequent inserts, may be positioned below first insert 130. As can be seen, the first insert 130 may act as a cover for any subsequent inserts that are located beneath it.

With reference to FIGS. 2-3, the system 110 may also include a variety of additional features. For example, the system 110 may include one or more container latches 150 for securing the first container portion 122 to the second container portion 124. The latch 150 may have tamper-proof elements to indicate that the sterilization container 120 has been opened and a sterilized environment has been compromised. Additionally, the container latch 150 may include or be integral with a gasket system or seal that creates a sterilization tight seal between the first and second container portions 122, 124. The system 110 may include an insert latch 152 that is removably engagable with the first and second inserts 130, 131. The insert latch 152 may retain first insert 130 nested on the second insert 131. The system 110 may also include one or more container handles 160 located on the sterilization container 120 for transporting the system 110. One or more insert handles (not shown) may also be included on the first and second inserts 130, 131 for inserting or removing the inserts 130, 131. Any handles on the first and second inserts 130, 131 may also function as stabilizing structures 170 that contribute to the proper fit or stacking of inserts when working with foot structures 172, as is discussed with respect to FIG. 4.

Figure 4:
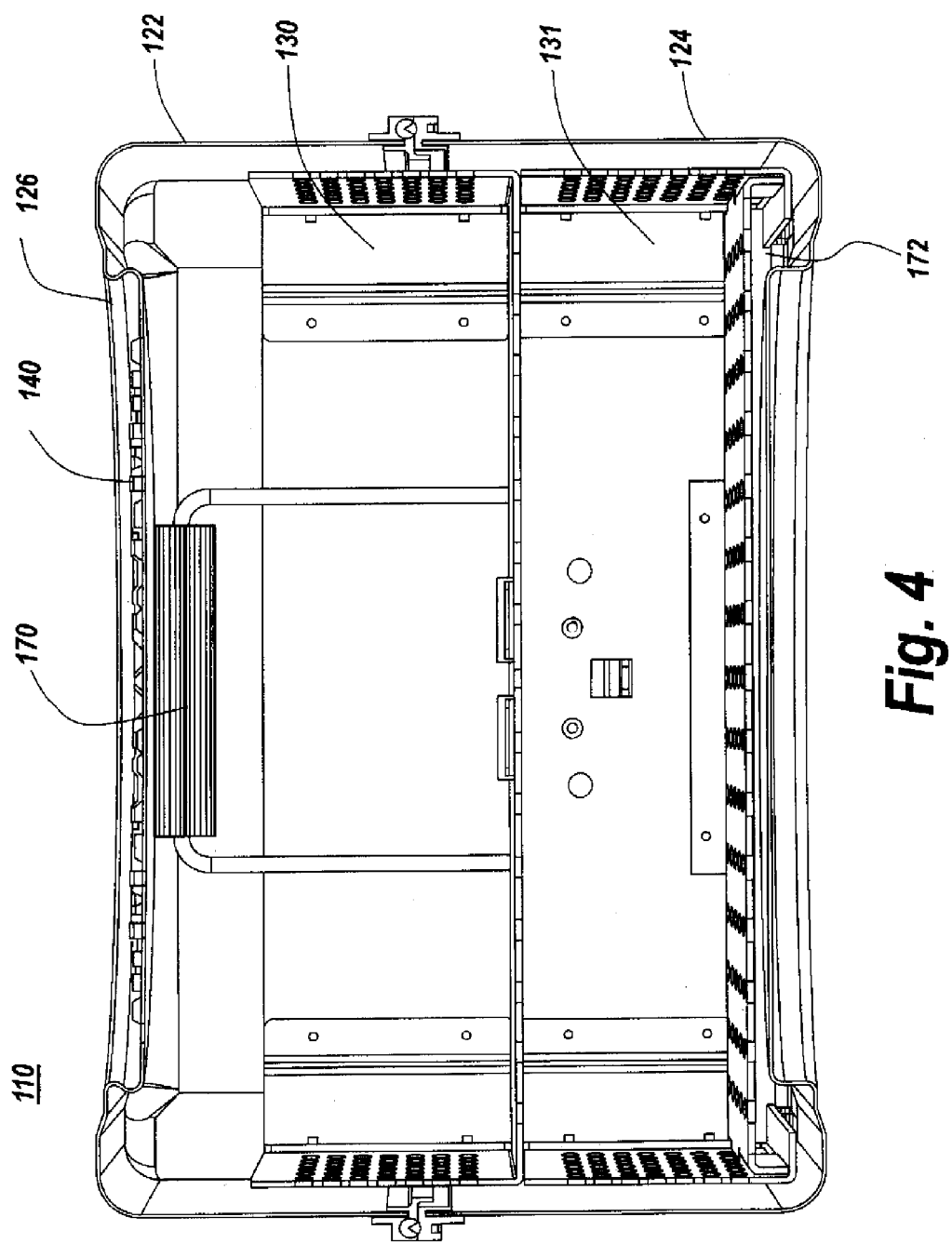
FIG. 4 is a side cross-sectional view illustration of the medical instrument sterilization system, in accordance with the second exemplary embodiment of the present disclosure.

FIG. 4 is a side cross-sectional view illustration of the medical instrument sterilization system 110, in accordance with the second exemplary embodiment of the present disclosure. The system 110 may also include a stabilizing structure 170 coupled to the first insert 130 and rising above each of the plurality of sidewalls 136 of the first insert 130. A foot structure 172 may be positioned on a bottom of the second insert 131. Together, the stabilizing structure 170 and the foot structure 172 may contact the first container portion 122 and the second container portion 124, respectively, to stabilize the first and second inserts 130, 131 within the interior compartment 128. This may prevent the first and second inserts 130, 131 from moving inside the sterilization container 120. The stabilizing structure 170 may be constructed from silicone or any other materials, and may have any configuration capable of substantially preventing movement of the first and second inserts 130, 131 by biasing the first and second inserts 130, 131 between the first and second container portions 122, 124 with the stabilizing structure 170 and the foot structure 172. Thus, when working in concert, both the stabilizing structure 170 and the foot structure 172 may prevent the first and second inserts 130, 131 from moving within the sterilization container 120 and being scratched, since scratches in first and second inserts 130, 131 may harbor bacteria and compromise a sterile environment.

Figure 5:
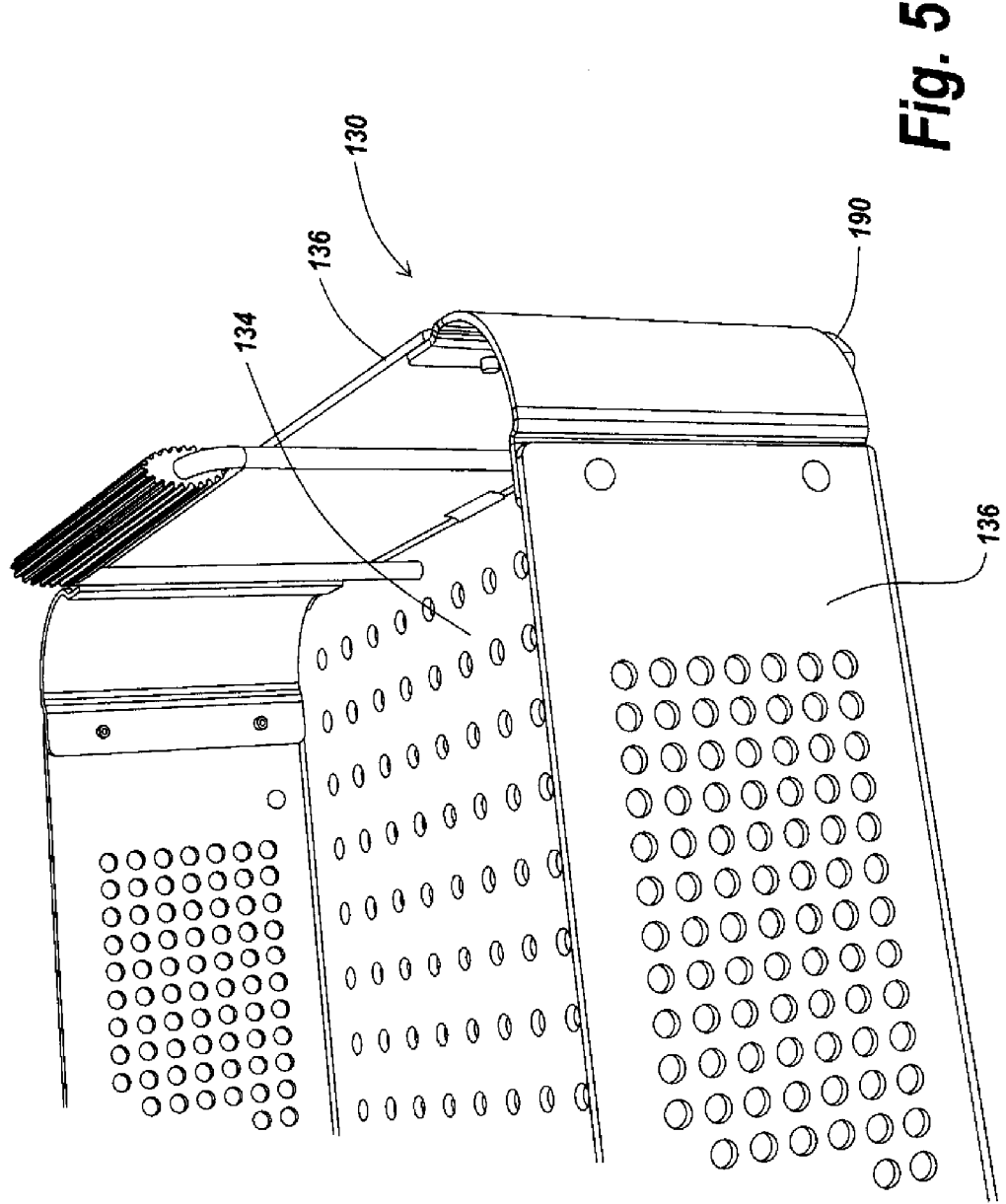
FIG. 5 is a plan view illustration of the first insert of the medical instrument sterilization system, in accordance with the second exemplary embodiment of the present disclosure.
Figure 6:
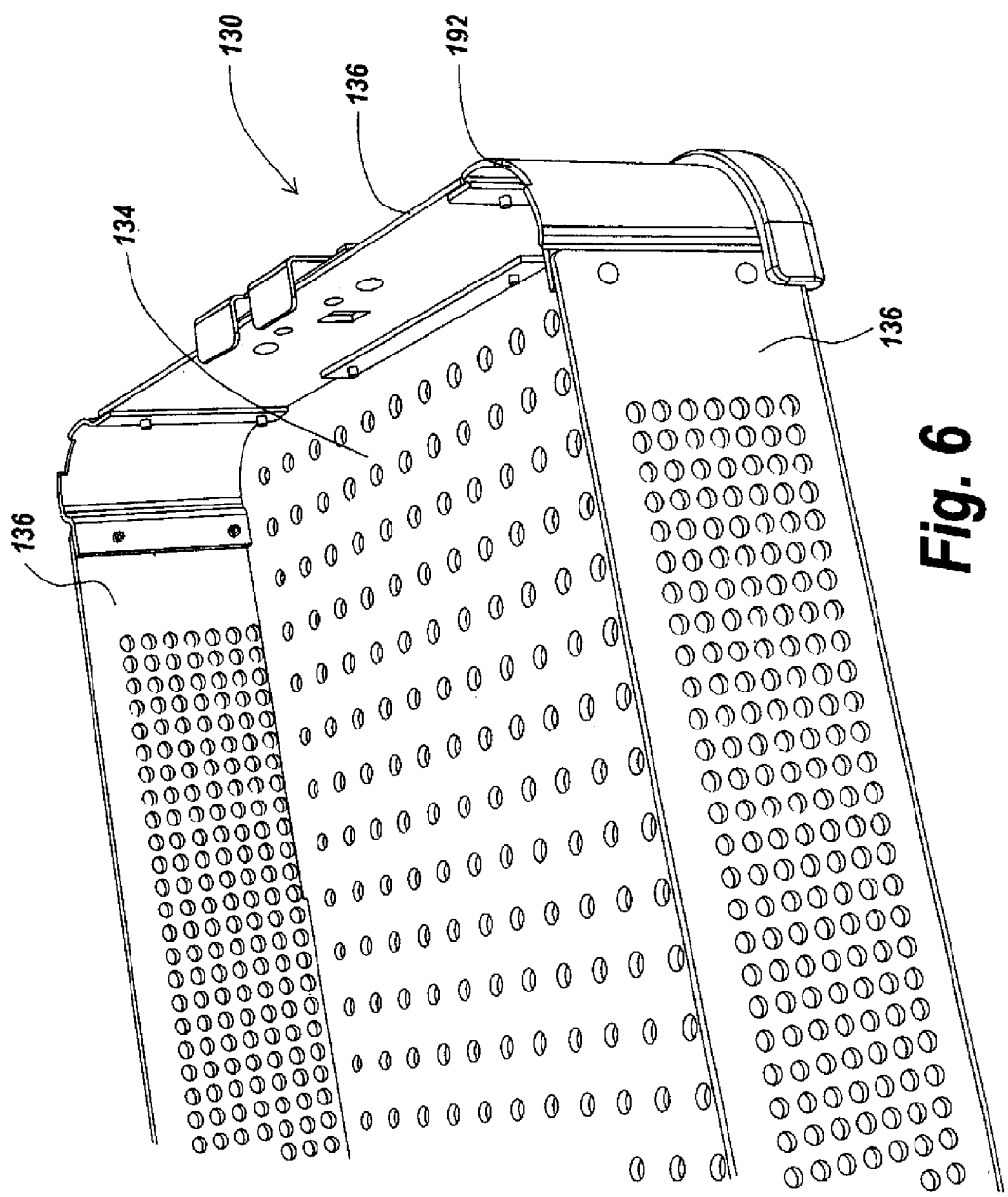
FIG. 6 is a plan view illustration of the second insert of the medical instrument sterilization system, in accordance with the second exemplary embodiment of the present disclosure.

FIG. 5 is a plan view illustration of the first insert 130 of the medical instrument sterilization system 110, in accordance with the second exemplary embodiment of the present disclosure and FIG. 6 is a plan view illustration of the second insert 131 of the medical instrument sterilization system 110, in accordance with the second exemplary embodiment of the present disclosure. As is shown in FIGS. 5-6, the system 110 may include a tab and slot system for facilitating nesting of the first and second inserts 130, 131. The tab and slot system may include a tab 190 formed on the first insert 130 and a slot 192 formed within one of the plurality of sidewalls 136 of the second insert 131. When the first insert 130 is positioned on top of the second insert 131, the tab 190 may engage with the slot 192. This engagement between the tab 190 and the slot 192 may nest the first insert 130 with the second insert 131, thereby preventing substantial lateral movement between the two structures. The tab 190 and the slot 192 may be positioned along any part of the first and second inserts 130, 131, respectively, but it may be preferable to position them at a corner of the first and second inserts 130, 131, as is shown in FIGS. 5-6.

Figure 7:
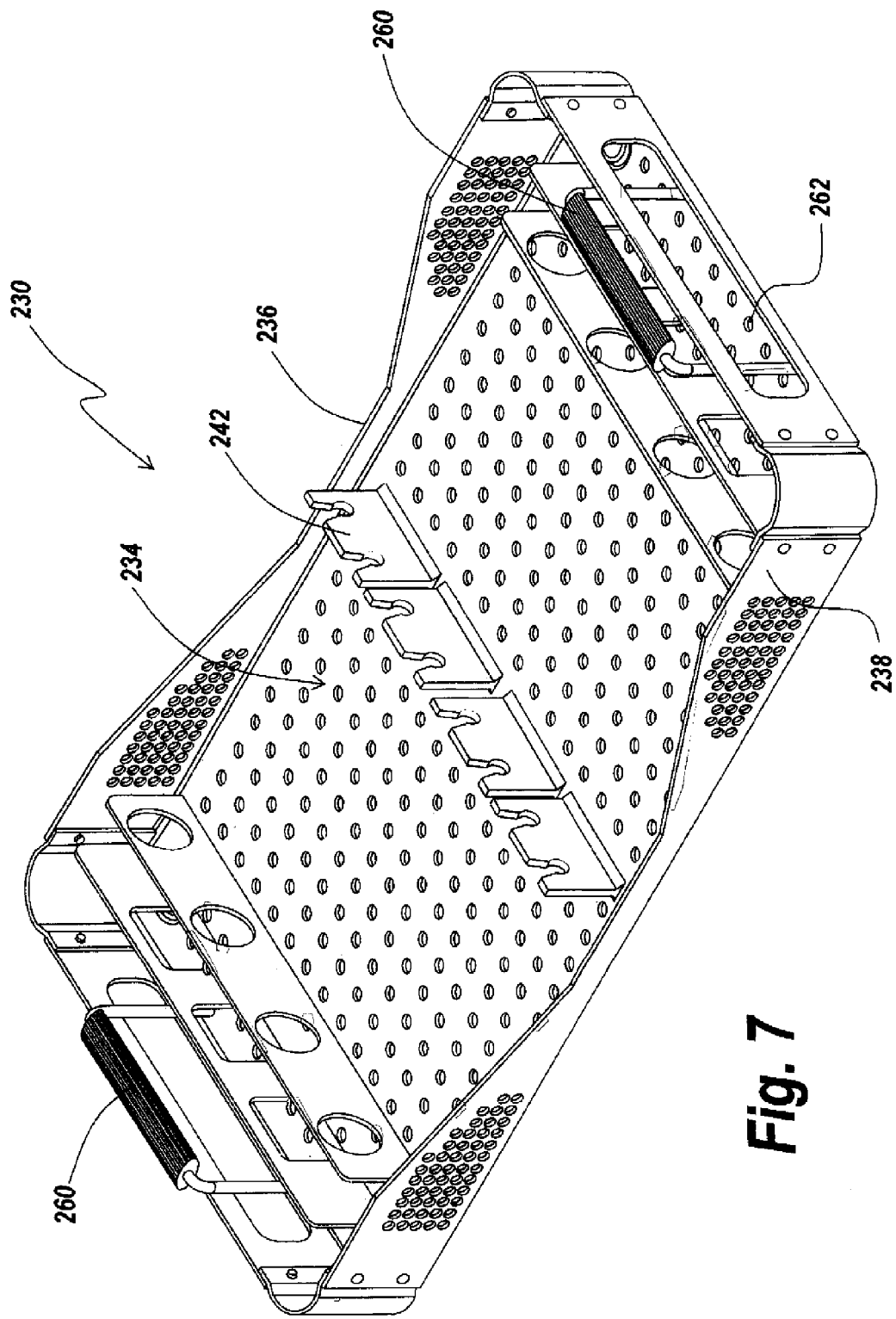
FIG. 7 is a plan view illustration of an insert of a medical instrument sterilization system, in accordance with a third exemplary embodiment of the present disclosure.

FIG. 7 is a plan view illustration of an insert 230 of a medical instrument sterilization system 210, in accordance with a third exemplary embodiment of the present disclosure. The third exemplary embodiment may include any of the components, features or designs of any of the embodiments disclosed herein. The insert 230 may have a variety of designs with a number of features. For example, the insert 230 may include partial walls 236 or full walls 238 with any type of perforations. The insert 230 may also include handles 260 and any number of cut-out portions 262. The medical instrument holding area 234 may be a substantially planar surface with a plurality of perforations that allow a sterilization substance to pass through the medical instrument holding area 234. Any number or type of instrument holding structures 242 may be included to position medical instruments. The medical instrument may engage with the holding structure 242, which in turn, is engaged with or affixed to the medical instrument holding area 234 of the insert 230. Other variations to the insert 230 may be employed, such as those with solely planar surfaces or those with no sidewalls in certain areas, all of which are considered within the scope of the present disclosure.

Figure 8:
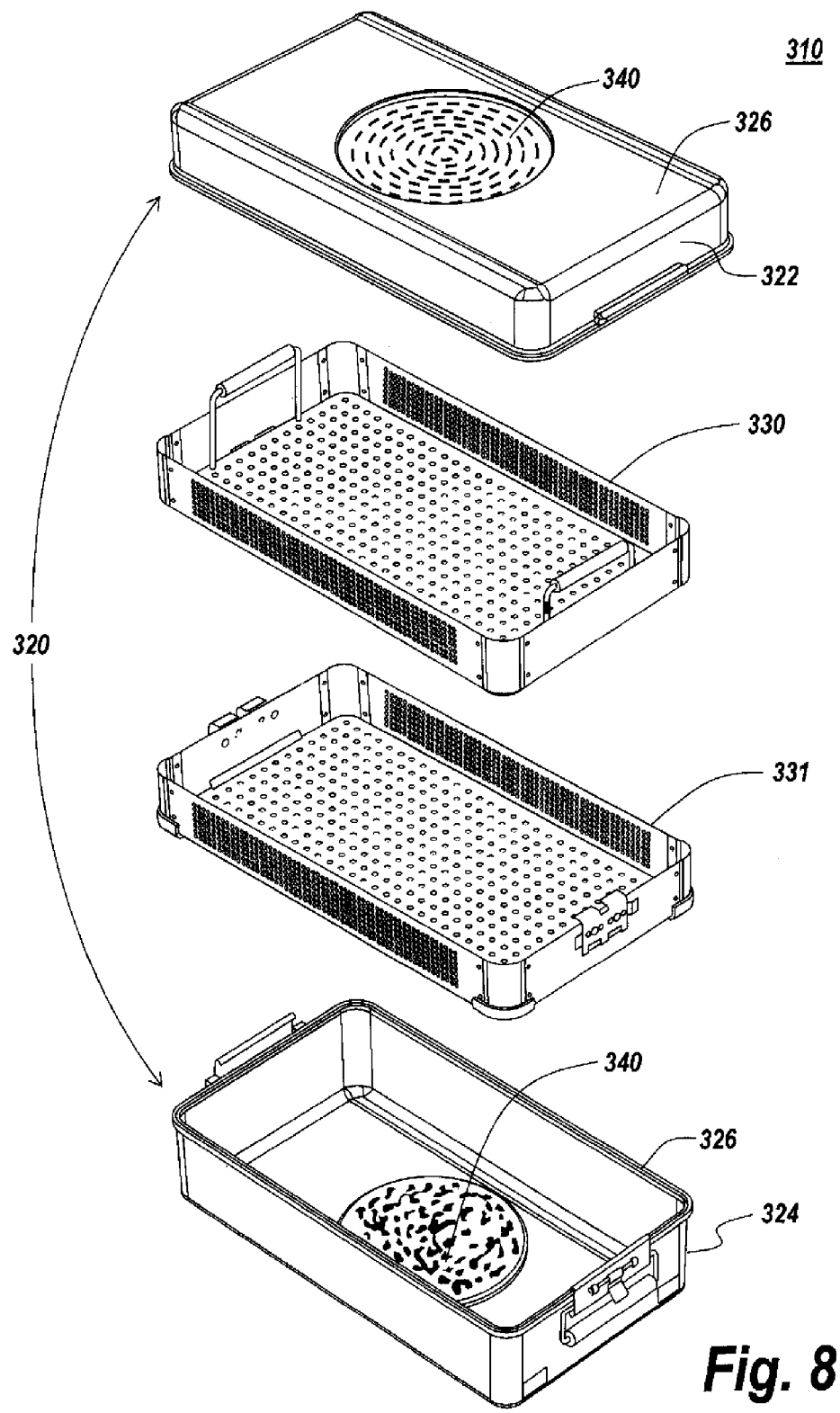
FIG. 8 is a plan view illustration of a medical instrument sterilization system, in accordance with a fourth exemplary embodiment of the present disclosure.

FIG. 8 is a plan view illustration of a medical instrument sterilization system 310, in accordance with a fourth exemplary embodiment of the present disclosure. The fourth exemplary embodiment may include any of the components, features or designs of any of the embodiments disclosed herein. The system 310 is substantially similar to the system 110 of the second exemplary embodiment, except that the system 310 includes two filters 340. Specifically, one filter 340 is positioned on the first container portion 322, towards a top of the sterilization container 320, and the other filter 340 may be positioned on an underside of the sterilization container 320.

Each of the filters 340 may be secured within a wall 326 of either the first container portion 322 or the second container portion 324. In FIG. 8, one filter 340 is depicted in the wall 326 of the first container portion 322 and another filter 340 is depicted within the wall 326 of the second container portion 324. During a sterilization process, the two or more filters 340 may allow a sterilization solution to enter and exit the sterilization container 320. For example, the sterilization solution may be sprayed from above the uppermost filter 340, and gravity may carry the sterilization solution through the sterilization container 320 to contact medical instruments on the first or second inserts 330, 331. The sterilization solution may then flow out the lowermost filter 340. No matter how many filters 340 are used or their location on the sterilization container 320, the filters 340 may function by allowing sterilization substances within an autoclave to pass through the filter 340 when it is wet, but prevent any substances, bacteria or microorganisms from passing through the filter 340 when it is dry.

Figure 9:
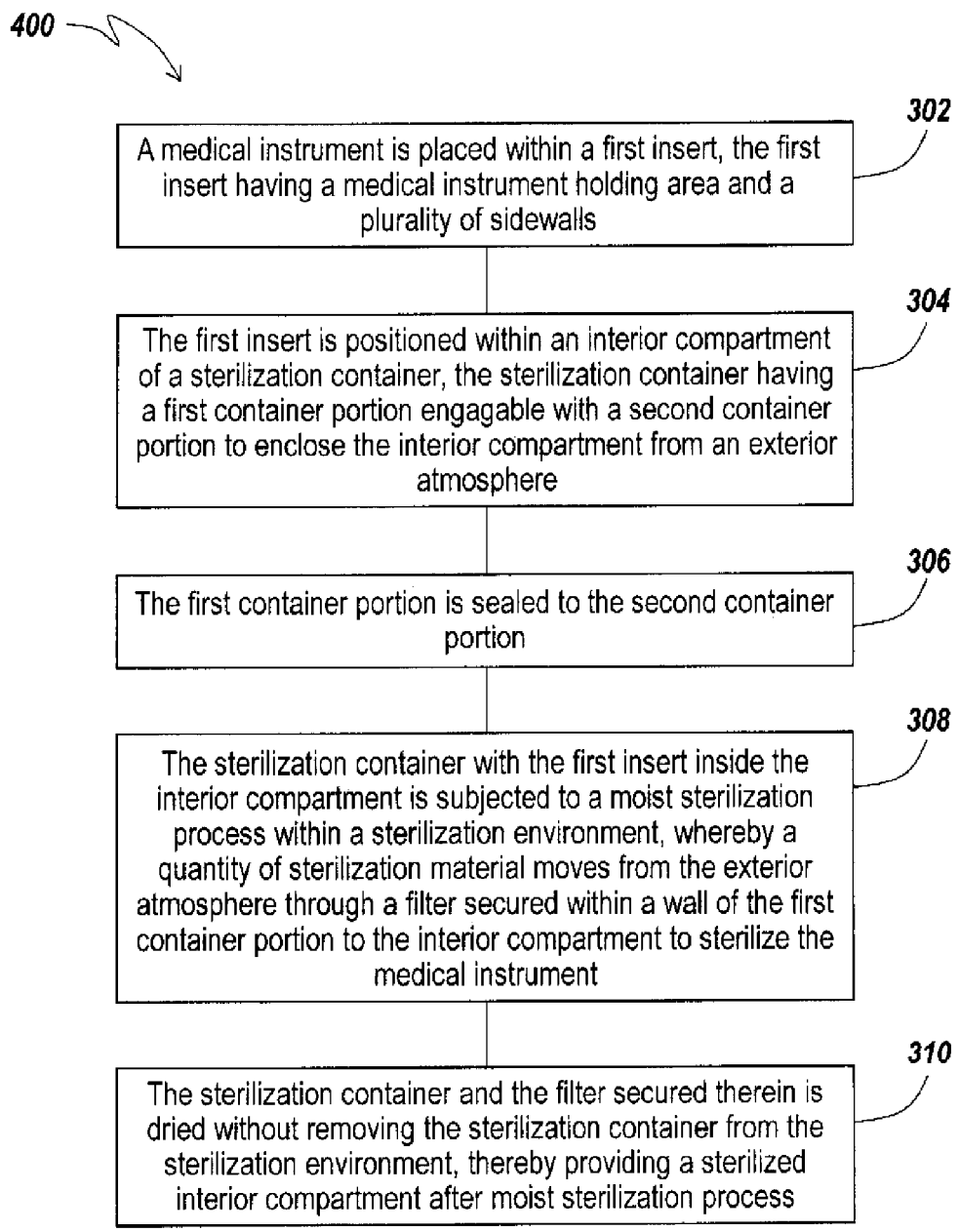
FIG. 9 is a flowchart illustrating a method of sterilizing a medical instrument with a medical instrument sterilization system, in accordance with the first exemplary embodiment of the disclosure.

FIG. 9 is a flowchart 400 illustrating a method of sterilizing a medical instrument with a medical instrument sterilization system 10 in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 402, a medical instrument is placed within a first insert 30, the first insert 30 having a medical instrument holding area 34 and a plurality of sidewalls 36. The first insert 30 is positioned within an interior compartment 28 of a sterilization container 20, the sterilization container 20 having a first container portion 22 engagable with a second container portion 24 to enclose the interior compartment 28 from an exterior atmosphere (block 404). The first container portion 22 is sealed to the second container portion 24 (block 406). The sterilization container 20 with the first insert 30 inside the interior compartment 28 is subjected to a moist sterilization process within a sterilization environment, whereby a quantity of sterilization material moves from the exterior atmosphere through a filter 40 secured within a wall 26 of the first container portion 22 to the interior compartment 28 to sterilize the medical instrument (block 408). The sterilization container 20 and the filter 40 secured therein is dried without removing the sterilization container 20 from the sterilization environment, thereby providing a sterilized interior compartment 28 after moist sterilization process (block 410).

The method may include any number of additional steps, processes, functions, or features disclosed with respect to any of the embodiments of this disclosure. For example, the sterilization container may be removed from the sterilization environment and stored without subjecting the interior compartment to a non-sterile material. The sterilization container with sterilized interior compartment may be stored for substantially any period of time without subjecting the interior compartment to a non-sterile material. This may include storing the sterilization container with sterilized interior compartment for more than 7, 14, 30, 60, or 90 days. Preferably, the sterilization container with sterilized interior compartment may be stored for 180 days or more without compromising the sterilized environment within the interior compartment.

To ensure that the inserts within the interior compartment remain in a proper place during the sterilization process, the inserts included may be nested together. This may include engaging a slot formed within one of the plurality of sidewalls of the second insert with a tab formed on the medical instrument holding area of the first insert. Likewise, a stabilizing configuration may be used where a stabilizing structure is coupled to the first insert, wherein the stabilizing structures rises above each of the plurality of sidewalls of the first insert, and a foot structure is positioned on the bottom of the second insert. The first and second inserts within the interior compartment may be substantially stabilized by contacting the first container portion with the stabilizing structure and the second container portion with the foot structure. During sterilization, the non-sterile material, such as bacteria or microorganisms, may pass through the filter when it is wet but be prevented from passing through the filter when it is dry. Of course, a number of additional steps may be included, such as those described within this disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medical instrument sterilization system comprising:
    a sterilization container having a first container portion engagable with a second container portion to enclose an interior compartment from an exterior atmosphere;
    at least a first and a second insert both locatable within the interior compartment of the sterilization container, wherein the first insert is nested on the second insert, the first and second insert having a medical instrument holding area surrounded by a plurality of sidewalls, wherein the medical instrument holding area is sized to hold at least one medical instrument; and
    a filter secured within a wall of the first container portion, wherein the filter is in communication with the interior compartment and the exterior atmosphere
    a stabilizing structure coupled to the first insert and rising above each of the plurality of sidewalls of the first insert; and
    a foot structure positioned on a bottom of the second insert, wherein the stabilizing structure and the foot structure contact the first container portion and the second container portion, respectively, to stabilize the first and second inserts within the interior compartment.

2. The medical instrument sterilization system of claim 1, wherein the medical instrument holding area has a fully open upper surface area.

3. The medical instrument sterilization system of claim 1, further comprising a plurality of medical instrument holding structures retained within the medical instrument holding area of at least one of the first and second inserts, wherein the at least one medical instrument is engageable within at least one of the plurality of medical instrument holding structures.

4. The medical instrument sterilization system of claim 1, wherein the filter prevents at least one of a bacteria and a microorganism from moving between the interior compartment and the exterior atmosphere.

5. The medical instrument sterilization system of claim 1, further comprising a second filter positioned within a wall of the second container portion, wherein the filter is in communication with the interior compartment and the exterior atmosphere.

6. The medical instrument sterilization system of claim 1, wherein the filter is a wet-functioning filter, wherein the wet-functioning filter allows a quantity of materials to move between the interior compartment and the exterior atmosphere when the filter is wet, and prevents the quantity of materials from moving between the interior compartment and the exterior atmosphere when the filter is dry.

7. The medical instrument sterilization system of claim 1, further comprising a container latch engaged between the first and second container portions, wherein the container latch seals the first container portion to the second container portion.

8. The medical instrument sterilization system of claim 1, further comprising a tab formed on the first insert and a slot formed within one of the plurality of sidewalls of the second insert, wherein the tab engages with the slot.

9. The medical instrument sterilization system of claim 8, wherein the tab and slot are positioned at a corner of the first and second inserts, respectively.

10. The medical instrument sterilization system of claim 1, further comprising a latch removably engagable with the first and second inserts, wherein the latch retains the first insert nested on the second insert.

11. A medical instrument sterilization system comprising:
    a sterilization container having a first container portion engagable with a second container portion to enclose an interior compartment from an exterior atmosphere;
    at least a first and a second insert positioned within the interior compartment of the sterilization container, wherein the first insert is positioned to nest on top of the second insert, wherein each of the first and second inserts have a medical instrument holding area surrounded by a plurality of sidewalls, wherein the medical instrument holding areas are sized to hold at least one medical instrument;
    a stabilizing structure coupled to the first insert and rising above each of the plurality of sidewalls of the first insert, the stabilizing structure further comprising a handle structure and a silicone stabilizing pad positioned on an upper portion of the handle structure;
    a foot structure positioned on a bottom of the second insert, wherein the silicone stabilizing pad of the stabilizing structure and the foot structure contact the first container portion and the second container portion, respectively, to stabilize the first and second inserts within the interior compartment; and a filter secured within a wall of the first container portion, wherein the filter is in communication with the interior compartment and the exterior atmosphere.

\* \* \* \* \*